United States Patent [19]

Ferrini et al.

[11] Patent Number: 5,321,027
[45] Date of Patent: Jun. 14, 1994

[54] SUBSTITUTED N-BENZOYL-N'-(2-PHENYLETHYL)-PIPERAZINES

[75] Inventors: Pier G. Ferrini, Binningen; Peter Burckhardt, Basel, both of Switzerland

[73] Assignee: Ciba-Geigy Corporation, Ardsley, N.Y.

[21] Appl. No.: 23,474

[22] Filed: Feb. 22, 1993

Related U.S. Application Data

[63] Continuation of Ser. No. 800,778, Nov. 27, 1991, abandoned.

[30] Foreign Application Priority Data

Dec. 5, 1990 [CH] Switzerland .................. 3838/90

[51] Int. Cl.$^5$ .................. A61K 31/495; C07D 295/16
[52] U.S. Cl. ....................... 514/255; 544/391
[58] Field of Search ................ 544/391; 514/255

[56] References Cited

U.S. PATENT DOCUMENTS

| | | | |
|---|---|---|---|
| 3,926,961 | 12/1975 | Ferrini et al. | 544/360 |
| 4,505,913 | 3/1985 | Ferrini et al. | 514/183 |
| 4,794,114 | 12/1988 | Benoer et al. | 514/333 |
| 4,804,661 | 2/1989 | Ferrini et al. | 514/255 |
| 5,011,928 | 4/1991 | Venero et al. | 544/391 |

FOREIGN PATENT DOCUMENTS

| | | |
|---|---|---|
| 250361 | 12/1987 | European Pat. Off. ....... 544/391 |
| 385043 | 9/1990 | European Pat. Off. . |
| 874096 | 8/1961 | United Kingdom . |

OTHER PUBLICATIONS

Jacob et al. C.A. 56:10165c (1962) Rhone-Poulenc.
Jacob et al. C.A. 57:15126h (1962) Rhone-Poulenc.
Jacob et al. C.A. 58:3444e (1963) Rhone-Poulenc.
Jacob et al. C.A. 58:4583f (1963) Rhone-Poulenc.
Jacob et al. C.A. 58:10211g (1963) Rhone-Poulenc.

*Primary Examiner*—Emily Bernhardt
*Attorney, Agent, or Firm*—Irving M. Fishman; Karen G. Kaiser

[57] ABSTRACT

N-Benzoyl-N'-(2-phenylethyl)-piperazines of formula I

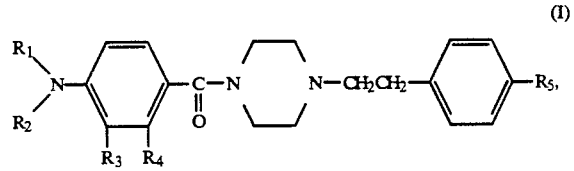

wherein $R_1$, $R_2$, $R_3$, $R_4$ and $R_5$ have the meanings as defined in the specification, and salts thereof, have analgesic properties and can be used as analgesic active ingredients in medicaments. They are prepared, for example, as follows: a compound of formula II

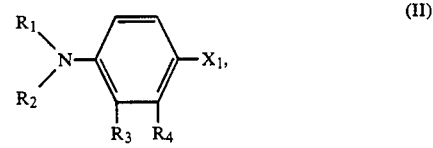

wherein $X_1$ is carboxy or reactive functionally modified carboxy, or a salt thereof, is reacted with a compound of formula III

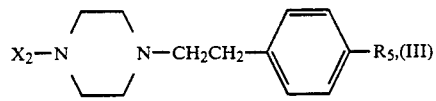

wherein $X_2$ is hydrogen.

20 Claims, No Drawings

SUBSTITUTED N-BENZOYL-N'-(2-PHENYLETHYL)-PIPERAZINES

This application is a continuation of application Ser. No. 07/800,778, filed Nov. 27, 1991 now abandoned.

The invention relates to novel N-benzoyl-N'-(2-phenylethyl)-piperazines of formula I

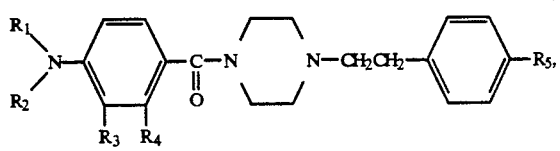

wherein $R_1$ is hydrogen, lower alkyl, lower alkanoyl, lower alkoxycarbonyl or lower alkenyloxycarbonyl, or a phenoxycarbonyl or phenyl-lower alkoxycarbonyl group that is unsubstituted or substituted by lower alkyl, lower alkoxy, halogen having an atomic number of up to and including 35, trifluoromethyl, nitro and/or by amino, $R_2$ is hydrogen or lower alkyl that is or is not interrupted by a nitrogen atom, $R_3$ and $R_4$, independently of one another, are hydrogen, lower alkyl or halogen having an atomic number of up to and including 35 and $R_5$ is halogen having an atomic number of up to and including 35, with the proviso that, in compounds of formula I wherein $R_5$ is chlorine and (a) $R_1$ is acetyl and $R_2$ is hydrogen or (b) $R_1$ and $R_2$ are both methyl, at least one of the radicals $R_3$ and $R_4$ is other than hydrogen, and their salts, to processes for their preparation, to pharmaceutical compositions comprising them and to their use as active ingredients in medicaments.

Lower alkyl interrupted by a nitrogen atom is, for example, N-mono- or N,N-di-lower alkylamino-lower alkyl.

Hereinbefore and hereinafter, lower radicals and compounds are to be understood as being, for example, radicals and compounds having up to and including 7, preferably up to and including 4, carbon atoms (C atoms).

Lower alkyl is, for example, $C_1-C_7$alkyl, preferably $C_1-C_4$alkyl, such as, especially, methyl or, secondly, ethyl, propyl, isopropyl or butyl, but may also be isobutyl, sec-butyl, tert-butyl or a $C_5-C_7$alkyl group, such as a pentyl, hexyl or heptyl group.

Lower alkanoyl is, for example, $C_1-C_7$alkanoyl, preferably $C_2-C_7$alkanoyl, such as formyl, acetyl, propionyl, butyryl, isobutyryl or valeroyl.

Lower alkoxycarbonyl is, for example, $C_1-C_7$alkoxycarbonyl, preferably $C_1-C_4$alkoxy-carbonyl, such as methoxy-, ethoxy-, propoxy-, isopropoxy- or tert-butoxy-carbonyl, but may also be isobutoxy-, sec-butoxy- or butoxy-carbonyl or a $C_5-C_7$alkoxycarbonyl group, such as a pentyloxy-, hexyloxy- or heptyloxy-carbonyl group.

Lower alkenyloxycarbonyl is, for example, $C_2-C_7$alkenyloxycarbonyl, preferably $C_3-C_5$alkoxycarbonyl, such as allyloxy- or methallyloxy-carbonyl, but may also be a butenyloxy-, pentenyloxy- or hexenyloxy-carbonyl group.

Phenyl-lower alkoxycarbonyl is, for example, phenyl-$C_1-C_7$alkoxycarbonyl, preferably phenyl-$C_1-C_4$alkoxycarbonyl, such as benzyloxycarbonyl, 1- or 2-phenylethoxycarbonyl, 3-phenylpropoxycarbonyl or 4-phenylbutoxycarbonyl, but may also be a phenyl-$C_5-C_7$alkoxycarbonyl group.

N-mono- or N,N-di-lower alkylamino-lower alkyl carries the N-mono- or N,N-di-lower alkylamino group especially in a position higher than the α-position and is, for example, N-$C_1-C_4$alkylamino-$C_2-C_7$alkyl, such as 2-methylaminoethyl, 2-ethylaminoethyl, 3-methylaminopropyl, 3-ethylaminopropyl or 4-methylaminobutyl, or, especially, N,N-di-$C_1-C_4$alkylamino-$C_1-C_7$alkyl, such as 2-dimethylaminoethyl, 2-diethylaminoethyl, 3-dimethylaminopropyl or 4-dimethylaminobutyl.

Halogen having an atomic number of up to and including 35 is, for example, chlorine or fluorine, and also bromine.

Salts of compounds of formula I are especially their acid addition salts, for example their pharmaceutically acceptable salts with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfaminic acids, for example methanesulfonates, benzenesulfonates, p-toluenesulfonates or N-cyclohexylsulfaminates (cyclamates), or salts with strong organic carboxylic acids, such as lower alkanecarboxylic acids or unsaturated or saturated aliphatic dicarboxylic acids which may be hydroxylated, for example acetates, oxalates, malonates, maleinates, fumarates, maleates, tartrates or citrates.

For isolation or purification purposes it is also possible to use pharmaceutically unsuitable salts. Only the pharmaceutically acceptable, non-toxic salts are used therapeutically and these salts are therefore preferred.

The compounds of formula I and their pharmaceutically acceptable salts have valuable pharmacological properties. In particular, they have pronounced analgesic activity. The analgesic activity can be demonstrated, for example, by the inhibition of phenyl-p-benzo-quinone-induced writhing syndrome in the mouse, for example in accordance with Agent and Actions 23, 29–31 (1988), at a dose of approximately 0.1 mg/kg p.o. and above, and in the rat by the inhibition of the experimental acetic acid writhing syndrome in accordance with Pain Res. and Therap. 1, 517 (1976), likewise at a dose of approximately 0.1 mg/kg p.o. and above.

The compounds of formula I and their pharmaceutically acceptable salts can accordingly be used as analgesic active ingredients in medicaments for the treatment of painful conditions of various origins, especially as peripheral analgesics.

In addition, the compounds of formula I and their pharmaceutically acceptable salts have a pronounced inhibitory effect on the biosynthesis of interleukin-1 (IL-1 belongs to the class of proinflammatory proteins and plays an important part, for example, in the synthesis of prostaglandins, the synthesis of neutral proteases by fibroplasts, synovial cells and chondrocytes, in the activation of endothelial cells and in inducing further proinflammatory cytokines, such as α-tumour necrosis factor (TNF) and interleukin-6 (IL-6). Furthermore, it stimulates bone resorption, regulates the body temperature of warm-blooded animals and regulates inter alia the development, activation, differentiation and proliferation of lymphocytes. Of especial therapeutic significance is the inhibitory effect of the compounds of formula I and their pharmaceutically acceptable salts on the biosynthesis of IL-1, TNF and IL-6. That effect can be demonstrated in vitro, for example using lipopolysaccharide-stimulated (LPS-stimulated) human monocytes in accordance with C. Rordorf-Adams et al., Drugs Exptl. Clin. Res. XV, 355-62 (1989) at a concentration of approximately 1 μ mol and above, and in vivo in the mouse by the inhibition of the LPS-induced formation of serum amyloid P (SAP) at an $ED_{50}$ of approximately from 1 to 15 mg/kg p.o. and in the rat by the lowering of LPS-induced artificial fever at an $ED_{50}$ of approximately from 0.05 to 3.5 mg/kg p.o.

Owing to those properties, the compounds of formula I and their pharmaceutically acceptable salts are excellently suitable for the therapeutic treatment of disorders in which overproduction of IL-1 by monocytic or macrophagous cell lines is causative or aggravating, such as inflammatory and degenerative diseases of the joints, for example rheumatoid arthritis, osteoarthrosis, psoriatic or infectious arthritis, Reiter's syndrome, gout and traumatic arthritis, and other acute or chronic inflammations, for example inflammatory gastric disorders, meningitis, skin diseases, such as psoriasis, Pemphigus vulgaris and the like, allergic skin reactions and autoimmune diseases, such as diabetes (type 1) and thyroiditis.

The invention relates, for example, to compounds of formula I wherein $R_1$ is hydrogen, lower alkyl or lower alkanoyl, $R_2$ is hydrogen, lower alkyl or N-mono- or N,N-di-lower alkylamino-lower alkyl, $R_3$ and $R_4$, independently of one another, are hydrogen, lower alkyl or halogen having an atomic number of up to and including 35 and $R_5$ is halogen having an atomic number of up to and including 35, with the proviso that, in compounds of formula I wherein $R_5$ is chlorine and (a) $R_1$ is acetyl and $R_2$ is hydrogen or (b) $R_1$ and $R_2$ are both methyl, at least one of the radicals $R_3$ and $R_4$ is other than hydrogen, and their salts.

The invention relates especially to compounds of formula I wherein $R_1$ is hydrogen, $C_1$–$C_4$alkyl, such as methyl or ethyl, $C_2$–$C_7$alkanoyl, such as acetyl, propionyl or valeroyl, $C_1$–$C_7$alkoxycarbonyl, preferably $C_1$–$C_4$alkoxycarbonyl, such as methoxy-, ethoxy-, propoxy-, isopropoxy- or tert-butoxy-carbonyl, or $C_2$–$C_7$alkenyloxycarbonyl, preferably $C_3$–$C_5$alkoxycarbonyl, such as allyloxy- or methallyloxy-carbonyl, or a phenoxycarbonyl or phenyl-$C_1$–$C_7$alkoxycarbonyl group, preferably a phenyl-$C_1$–$C_4$alkoxycarbonyl group, that is unsubstituted or substituted by lower alkyl, lower alkoxy, halogen having an atomic number of up to and including 35, trifluoromethyl, nitro and/or by amino, such as benzyloxycarbonyl, 1- or 2-phenylethoxycarbonyl, 3-phenylpropoxycarbonyl or 4-phenylbutoxycarbonyl, $R_2$ is hydrogen, $C_1$–$C_4$alkyl, such as methyl or ethyl, N-$C_1$–$C_4$alkylamino-$C_2$–$C_7$alkyl, such as 2-methylaminoethyl, 2-ethylaminoethyl, 3-methylaminopropyl, 3-ethylaminopropyl or 4-methylaminobutyl, or, especially, N,N-di-$C_1$–$C_4$alkylamino-$C_1$–$C_7$alkyl, such as 2-dimethylaminoethyl, 2-diethylaminoethyl, 3-dimethylaminopropyl or 4-dimethylaminobutyl, one of the radicals $R_3$ and $R_4$ is hydrogen, $C_1$–$C_4$alkyl, such as methyl, or halogen having an atomic number of up to and including 35, such as fluorine or chlorine, and the other is hydrogen and $R_5$ is halogen having an atomic number of up to and including 35, such as fluorine, chlorine or bromine, with the proviso that, in compounds of formula I wherein $R_5$ is chlorine and (a) $R_1$ is acetyl and $R_2$ is hydrogen or (b) $R_1$ and $R_2$ are both methyl, at least one of the radicals $R_3$ and $R_4$ is other than hydrogen, and their salts, especially their pharmaceutically acceptable salts.

The invention relates more especially, for example, to compounds of formula I wherein $R_1$ is hydrogen, $C_1$–$C_4$alkyl, such as methyl or ethyl, or $C_2$–$C_7$alkanoyl, such as acetyl, propionyl or valeroyl, $R_2$ is hydrogen or $C_1$–$C_4$alkyl, such as methyl or ethyl, one of the radicals $R_3$ and $R_4$ is hydrogen, $C_1$–$C_4$alkyl, such as methyl, or halogen having an atomic number of up to and including 35, such as fluorine or chlorine, and the other is hydrogen and $R_5$ is halogen having an atomic number of up to and including 35, such as fluorine, chlorine or bromine, with the proviso that, in compounds of formula I wherein $R_5$ is chlorine and (a) $R_1$ is acetyl and $R_2$ is hydrogen or (b) $R_1$ and $R_2$ are both methyl, at least one of the radicals $R_3$ and $R_4$ is other than hydrogen, and their salts, especially their pharmaceutically acceptable salts.

The invention relates very especially to compounds of formula I wherein $R_1$ is hydrogen, $C_2$–$C_7$alkanoyl, such as acetyl, propionyl or valeroyl, $C_1$–$C_4$alkoxycarbonyl, such as ethoxycarbonyl, $C_3$–$C_5$alkenyloxycarbonyl, such as allyloxycarbonyl, phenoxycarbonyl or phenyl-$C_1$–$C_4$alkoxycarbonyl, such as benzyloxycarbonyl, $R_2$ is hydrogen, $C_1$–$C_4$alkyl, such as methyl or ethyl, or N,N-di-$C_1$–$C_4$alkylamino-$C_1$–$C_7$alkyl, such as 2-dimethylaminoethyl, 2-diethylaminoethyl, 3-dimethylaminopropyl or 4-dimethylaminobutyl, one of the radicals $R_3$ and $R_4$ is hydrogen, $C_1$–$C_4$alkyl, such as methyl, or halogen having an atomic number of up to and including 35, such as fluorine or chlorine, and the other is hydrogen and $R_5$ is halogen having an atomic number of up to and including 35, such as fluorine, chlorine or bromine, with the proviso that, in compounds of formula I wherein $R_5$ is chlorine and $R_1$ is acetyl and $R_2$ is hydrogen, at least one of the radicals $R_3$ and $R_4$ is other than hydrogen, and their salts, especially their pharmaceutically acceptable salts.

Of especial interest are compounds of formula I wherein $R_1$ is $C_1$–$C_4$alkanoyl, such as acetyl or propionyl, and $R_2$ is hydrogen or $C_1$–$C_4$alkyl, such as methyl or ethyl, or $R_1$ and $R_2$ are both hydrogen, $R_3$ is hydrogen or $C_1$–$C_4$alkyl, such as methyl, and $R_4$ is hydrogen, or $R_3$ is hydrogen and $R_4$ is halogen having an atomic number of up to and including 35, such as chlorine or bromine, and $R_5$ is halogen having an atomic number of up to and including 35, such as fluorine, chlorine or bromine, with the proviso that, in compounds of formula I wherein $R_5$ is chlorine and $R_1$ is acetyl and $R_2$ is hydrogen, at least one of the radicals $R_3$ and $R_4$ is other than hydrogen, and their salts, especially their pharmaceutically acceptable salts.

Of very especial interest are compounds of formula I wherein $R_1$ is hydrogen or $C_1$–$C_4$alkanoyl, such as acetyl or propionyl, $R_2$ is hydrogen, $R_3$ is $C_1$–$C_4$alkyl, such as methyl, and $R_4$ is hydrogen, or $R_3$ is hydrogen and $R_4$ is halogen having an atomic number of up to and including 35, such as fluorine, chlorine or bromine, with the proviso that, in compounds of formula I wherein $R_5$ is chlorine and $R_1$ is acetyl and $R_2$ is hydrogen, at least one of the radicals $R_3$ and $R_4$ is other than hydrogen, and their salts, especially their pharmaceutically acceptable salts.

On the one hand, the invention relates preferably to compounds of formula I wherein $R_1$ is hydrogen, $R_2$ is hydrogen or $C_1$–$C_4$alkyl, such as methyl or ethyl, one of the radicals $R_3$ and $R_4$ is hydrogen, $C_1$–$C_4$alkyl, such as methyl, or halogen having an atomic number of up to and including 35, such as fluorine or chlorine, and the other is hydrogen and $R_5$ is halogen having an atomic number of up to and including 35, such as fluorine, chlorine or bromine, and their salts, especially their pharmaceutically acceptable salts.

On the other hand, the invention relates preferably to compounds of formula I wherein $R_1$ is $C_2-C_7$alkanoyl, such as acetyl, propionyl or valeroyl, $R_2$ is hydrogen or $C_1-C_4$alkyl, such as methyl or ethyl, $R_3$ is hydrogen, $R_4$ is hydrogen or halogen having an atomic number of up to and including 35, such as chlorine, and $R_5$ is halogen having an atomic number of up to and including 35, such as chlorine or bromine, with the proviso that, in compounds of formula I wherein $R_5$ is chlorine and $R_1$ is acetyl and $R_2$ is hydrogen, at least one of the radicals $R_3$ and $R_4$ is other than hydrogen, and their salts, especially their pharmaceutically acceptable salts.

On the one hand, the invention relates especially to compounds of formula I wherein $R_1$ is hydrogen, $R_2$ is hydrogen or $C_1-C_4$alkyl, such as methyl or ethyl, $R_3$ is hydrogen or $C_1-C_4$alkyl, such as methyl, $R_4$ is hydrogen, fluorine or chlorine and $R_5$ is fluorine, chlorine or bromine, and their salts, especially their pharmaceutically acceptable salts.

On the other hand, the invention relates especially to compounds of formula I wherein $R_1$ is $C_2-C_7$alkanoyl, such as acetyl, propionyl or valeroyl, or phenyl-$C_1-C_4$alkoxycarbonyl, such as benzyloxycarbonyl, $R_2$ is hydrogen, $C_1-C_4$alkyl, such as methyl or ethyl, or N,N-di-$C_1-C_4$alkylamino-$C_1-C_7$alkyl, such as 2-dimethylaminoethyl, $R_3$ and $R_4$ are hydrogen and $R_5$ is chlorine, with the proviso that, in compounds of formula I wherein $R_5$ is chlorine and $R_1$ is acetyl and $R_2$ is hydrogen, at least one of the radicals $R_3$ and $R_4$ is other than hydrogen, and their salts, especially their pharmaceutically acceptable salts.

The invention relates very especially, for example, to compounds of formula I wherein $R_1$ is $C_2-C_7$alkanoyl, such as acetyl, propionyl or valeroyl, $R_2$ is hydrogen or $C_1-C_4$alkyl, such as methyl or ethyl, $R_3$ and $R_4$ are hydrogen and $R_5$ is chlorine, with the proviso that, in compounds of formula I wherein $R_5$ is chlorine and $R_1$ is acetyl and $R_2$ is hydrogen, at least one of the radicals $R_3$ and $R_4$ is other than hydrogen, and their salts, especially their pharmaceutically acceptable salts.

The invention relates most especially to compounds of formula I wherein $R_1$ is hydrogen, $R_2$ is hydrogen or, secondly, $C_1-C_4$alkyl, such as methyl or ethyl, $R_3$ is hydrogen and $R_4$ is fluorine or chlorine, or $R_3$ is methyl and $R_4$ is hydrogen, and $R_5$ is fluorine, chlorine or bromine, and their salts, especially their pharmaceutically acceptable salts.

The invention relates specifically to the compounds of formula I mentioned in the Examples and to their salts, especially their pharmaceutically acceptable salts.

The process for the preparation of the compounds of formula I is based on methods known per se and comprises:

a) reacting a compound of formula II

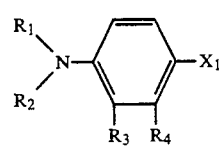

(II)

wherein $X_1$ is carboxy or reactive functionally modified carboxy, or a salt thereof, with a compound of formula III

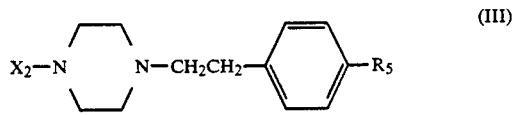

(III)

wherein $X_2$ is hydrogen or an amino-protecting group, or b) reacting a compound of formula IV

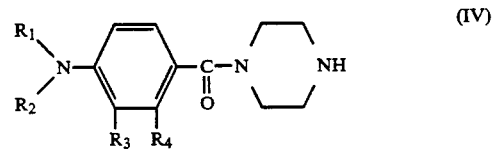

(IV)

or a salt thereof, with a compound of formula V

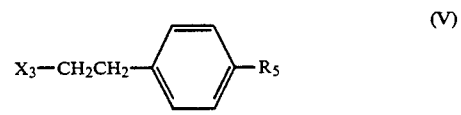

(V)

wherein $X_3$ is hydroxy or reactive esterified hydroxy, or c) cyclising a compound of formula VI

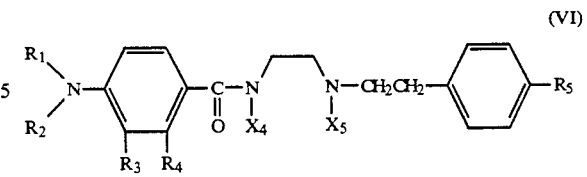

(VI)

wherein one of the radicals $X_4$ and $X_5$ is hydrogen and the other is a group of the formula —$CH_2$—$CH_2$—$X_3$ (VIa) and $X_3$ is hydroxy or reactive esterified hydroxy, or d) oxidising a compound of formula VII

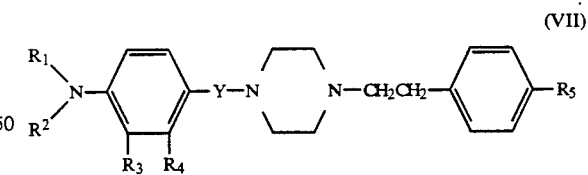

(VII)

wherein Y is a group that can be oxidised to form carbonyl, and, if desired, converting a compound obtainable in accordance with the process or by a different method into a different compound of formula I, separating a mixture of isomers obtainable in accordance with the process into the components, converting a free compound of formula I obtainable in accordance with the process into a salt and/or converting a salt obtainable in accordance with the process into the free compound of formula I or into a different salt.

The reactions described hereinbefore and hereinafter are carried out in a manner known per se, for example in the absence or, customarily, in the presence of a suitable solvent or diluent or of a mixture thereof, and, as required, with cooling, at room temperature or with heating, for example in a temperature range of from approximately −78° to the boiling temperature of the reaction medium, preferably from approximately −10° to approximately 150° C., and, if necessary, in a closed vessel, under pressure, in an inert gas atmosphere and-/or under anhydrous conditions.

In the starting materials, the basic centre may be, for example, in the form of acid addition salts, for example with the acids listed above in connection with salts of compounds of formula I, while starting compounds of formula II wherein $X_1$ is carboxy can form salts with bases. Suitable salts with bases are, for example, corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-hydroxy-$C_1$–$C_7$alkylamines, hydroxy-$C_1$–$C_7$alkyl-$C_1$–$C_7$alkylamines or polyhydroxy-$C_4$–$C_7$alkylamines. Cyclic amines are, for example, morpholine, thiomorpholine, piperidine or pyrrolidine. Examples of suitable mono-$C_1$–$C_7$alkylamines are ethylamine or tert-butylamine, examples of suitable di-$C_1$–$C_7$alkylamines are diethylamine or diisopropylamine, and examples of suitable tri-$C_1$–$C_7$alkylamines are trimethylamine or triethylamine. Suitable hydroxy-$C_1$–$C_7$alkylamines are, for example, mono-, di- and tri-ethanolamines, and suitable hydroxy-$C_1$–$C_7$alkyl-$C_1$–$C_7$alkylamines are, for example, N,N-dimethylamino- or N,N-diethylamino-ethanol, and an example of a suitable polyhydroxy-$C_6$alkylamine is glucosamine.

Reactive functionally modified carboxy $X_1$ is, for example, esterified, especially reactive esterified, carboxy, anhydridised carboxy or amidated carboxy.

Esterified carboxy is, for example, unsubstituted or substituted $C_1$–$C_7$alkoxycarbonyl, such as ethoxycarbonyl, but is preferably reactive esterified carboxy, for example vinyloxycarbonyl that is optionally additionally activated, for example, by $C_1$–$C_7$alkoxy or by unsubstituted or substituted carbamoyl, such as 1-$C_1$–$C_7$alkoxy-, for example 1-ethoxyvinyloxycarbonyl, or 2-(N-$C_1$–$C_7$alkylcarbamoyl)-, for example 2-(N-ethylcarbamoyl)-vinyloxycarbonyl, and phenoxy- or thiophenoxy-carbonyl that is unsubstituted or substituted, for example, by nitro, halogen, $C_1$–$C_7$alkanesulfonyl or by phenylazo, such as 4-nitro-, 2,4,5-trichloro-, pentachloro-, 4-methanesulfonyl-, 4-phenylazo-phenoxy-carbonyl, thiophenoxy- or 4-nitrothiophenoxy-carbonyl, and similarly activated methoxycarbonyl, for example methoxycarbonyl substituted by cyano or by free or esterified carboxy, especially cyanomethoxycarbonyl. Reactive esterified carboxy may also be 1,1-or 1,3-disubstituted 2-isoureidocarbonyl, such as 1,1-di-lower alkyl-, 1,1-diaryl- or 1,1-diaryl-$C_1$–$C_7$alkyl-2-isoureidocarbonyl, for example 1,1-diethyl-, 1,1-diphenyl- or 1,1-dibenzyl-2-isoureidocarbonyl, or 1,3-dicycloalkyl-2-isoureidocarbonyl, for example 1,3-dicyclohexyl-2-isoureidocarbonyl, or N-$C_2$–$C_7$alkyleneaminooxycarbonyl, such as N-piperidinyloxycarbonyl, and N-imidooxycarbonyl, for example N-succinimidooxy-or N-phthalimidooxy-carbonyl.

By anhydridised carboxy there is to be understood, for example, straight-chained or branched $C_1$–$C_7$alkoxycarbonyloxycarbonyl, such as ethoxy- or isobutoxycarbonyloxycarbonyl, halocarbonyl, such as chlorocarbonyl, azidocarbonyl, halophosphoryloxycarbonyl, such as dichlorophosphoryloxycarbonyl, or unsubstituted or substituted, for example halo- or aryl-substituted, $C_1$–$C_7$alkanoyloxycarbonyl, such as pivaloyloxy-, trifluoroacetyloxy- or phenylacetoxy-carbonyl.

Reactive amidated carboxy is, for example, unsubstituted or substituted, for example $C_1$–$C_7$alkyl-substituted, 1-imidazolylcarbonyl or 1-pyrazolylcarbonyl, such as 3,5-dimethylpyrazolylcarbonyl.

An amino-protecting group $X_2$ is, for example, acyl, such as $C_1$–$C_7$alkanoyl, for example formyl or acetyl, halocarbonyl, such as chlorocarbonyl, also unsubstituted or substituted aryl- or heteroaryl-sulfonyl, such as 2-pyridyl- or 2-nitrophenyl-sulfonyl.

Hereinbefore and hereinafter, in the description of the processes, reactive esterified hydroxy, for example $X_3$, unless otherwise defined, is especially hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, unsubstituted or substituted, for example halo-substituted, $C_1$–$C_7$alkanesulfonyloxy, for example methane- or trifluoromethane-sulfonyloxy, $C_3$–$C_7$cycloalkanesulfonyloxy, for example cyclohexanesulfonyloxy, or unsubstituted or substituted, for example $C_1$–$C_7$alkyl-substituted or halo-substituted, benzenesulfonyloxy, for example p-bromophenyl- or p-toluene-sulfonyloxy.

If, for example, bases are used in the reactions described hereinbefore and hereinafter, there are suitable, for example, unless otherwise indicated, alkali metal hydroxides, hydrides, amides, alkanolates, carbonates, triphenylmethylides, di-$C_1$–$C_7$alkylamides, amino-$C_1$–$C_7$alkylamides or $C_1$–$C_7$alkylsilylamides, naphthylamines, $C_1$–$C_7$alkylamines, basic heterocycles, ammonium hydroxides and carbocyclic amines. There may be mentioned by way of example lithium hydroxide, sodium hydroxide, hydride, amide or ethoxide, potassium tert-butoxide or carbonate, lithium triphenylmethylide or diisopropylamide, potassium 3-(aminopropyl)-amide, potassium bis(trimethylsilyl)amide, dimethylaminonaphthalene, di- or tri-ethylamine, pyridine, benzyltrimethylammonium hydroxide, 1,5-diazabicyclo[4.3.0]non-5-ene (DBN) and 1,8-diaza-bicyclo[5.4.0]undec-7-ene (DBU).

Variant a): The N-acylation according to the process is carried out in a manner known per se, if necessary in the presence of a condensation agent, especially a basic condensation agent. Suitable bases are, for example, representatives of the bases listed above. The basicity of the compound of formula III is also often sufficient.

If $X_1$ is carboxy, there are formed initially, for example, the corresponding ammonium salts, which can be dehydrated by heating or by treatment with suitable dehydrating agents (as condensation agents), such as carbodiimides, for example N,N'-di-lower alkyl- or N,N'-dicycloalkyl-carbodiimide, such as N,N'-diethyl-, N,N'-diisopropyl- or N,N'-dicyclohexyl-carbodiimide, advantageously with the addition of N-hydroxysuccinimide or unsubstituted or substituted, for example halo-, lower alkoxy- or lower alkyl-substituted, 1-hydroxybenzotriazole or N-hydroxy-5-norbornene-2,3-dicarboxamide, and N,N-carbonyldiimidazole. When carbodiimides are used, for example the corresponding 1-isoureidocarbonyl compounds may also be formed as intermediates. There may also be used as water-binding condensation agents N-ethoxycarbonyl-2-ethoxy-1,2-dihydroquinoline, phosphoryl cyanamides or azides, such as diethylphosphoryl cyanamide or diphenylphosphoryl azide, triphenylphosphine disulfide or 1-lower alkyl-2-halopiperidinium halides, such as 1-methyl-2-chloropyridinium iodide.

Some of the starting materials used in this process variant are known, or they can be prepared in accordance with processes known per se.

For the preparation of compounds of formula II wherein $X_1$ is unsubstituted or substituted $C_1$-$C_7$alkoxycarbonyl it is normally possible to use as starting material the free acid ($X_1$=carboxy) or an acid anhydride ($X_1$ is, for example, halocarbonyl) and to react them, for example, with the corresponding alcohol, if necessary in reactive form, for example a $C_1$-$C_7$alkyl halide. The preparation of compounds of formula II wherein $X_1$ is optionally additionally activated vinyloxycarbonyl can be carried out, for example, by transesterification of a $C_1$-$C_7$alkyl ester with vinyl acetate (activated vinyl ester method), by reaction of the free acid of a compound of formula II with lower alkoxyacetylene (for example ethoxyacetylene method) or, by analogy with the Woodward method, with a 1,2-oxazolium salt. The preparation of compounds of formula II comprising an unsubstituted or substituted phenoxy- or thiophenoxycarbonyl group can be carried out, for example, using the free acid as starting material, in accordance with the carbodiimide method by reaction with the corresponding (thio-)phenol. Likewise using the free acid of formula II as starting material, compounds of formula II wherein $X_1$ is activated methoxycarbonyl or 1,1- or 1,3-disubstituted 2-isoureidocarbonyl can be obtained, for example, by reaction with a haloacetonitrile, such as chloroacetonitrile (cyanomethyl ester method), or with a carbodiimide or cyanamide (carbodiimide or cyanamide method). The preparation of N-$C_2$-$C_7$alkyleneaminooxycarbonyl and N-imidooxycarbonyl compounds of formula II can be carried out, for example, using the free acid of formula II from corresponding N-hydroxy compounds using carbodiimides in accordance with the activated N-hydroxy esters method. For the preparation of compounds of formula II wherein $X_1$ is straight-chained or branched $C_1$-$C_7$alkoxycarbonyloxycarbonyl, halophosphoryloxycarbonyl or unsubstituted or substituted $C_1$-$C_7$alkanoyloxycarbonyl, there may be used as starting material, for example, a free acid of formula II which can be treated, for example, with a corresponding halide, such as an unsubstituted or substituted $C_1$-$C_7$alkylcarbonic acid halide (mixed O-carbonic acid anhydrides method), phosphorus oxyhalide (for example phosphorus oxychloride method) or unsubstituted or substituted $C_1$-$C_7$alkanoyl halide (mixed carboxylic acid halides method). Azidocarbonyl compounds of formula II are obtainable, for example, by treating corresponding hydrazides with nitrous acid (azide method). For the preparation of compounds of formula II wherein $X_1$ is unsubstituted or substituted 1-imidazolylcarbonyl or 1-pyrazolylcarbonyl, the free acid of formula II is reacted, for example, with di-(1-imidazolyl)-carbonyl (imidazolide method) or the relevant hydrazide is reacted, for example, with a corresponding 1,3-diketone (pyrazolide method).

Variant b): The radical $X_3$ is especially reactive esterified hydroxy, preferably halogen, such as chlorine.

The N-alkylation according to the process is carried out in a manner known per se, if necessary in the presence of a base, for example one of the bases listed above.

Some of the starting materials used in this process variant are known, or they can be prepared in a manner known per se.

For example, the starting material of formula IV can be prepared by reacting a compound of the formula

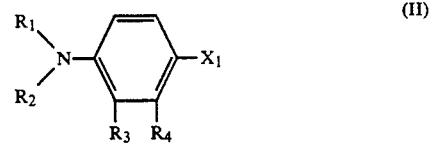

wherein $X_1$ is carboxy or reactive functionally modified carboxy, or a salt thereof, in the manner described in Variant a) with a compound of the formula

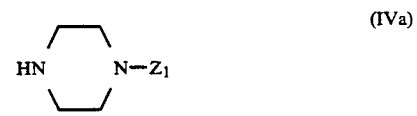

wherein $Z_1$ is hydrogen or an amino-protecting group, such as benzyl, or a salt thereof, and, if desired, removing the amino-protecting group, for example benzyl, by means of conventional hydrogenolysis.

Variant c): The cyclisation (intramolecular N-alkylation) according to the process is carried out in a manner known per se, if necessary in the presence of a condensation agent, especially a basic condensation agent. The bases used are, for example, those listed above.

$X_3$ in that case is especially reactive esterified hydroxy, preferably halogen, such as chlorine.

The starting material can be prepared in a manner known per se. For example, a compound of the formula

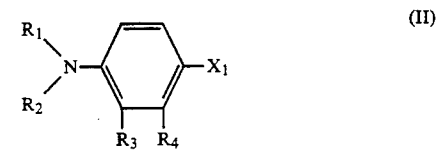

wherein $X_1$ is carboxy or reactive functionally modified carboxy, or a salt thereof, is used as starting material and is reacted first with a compound of the formula

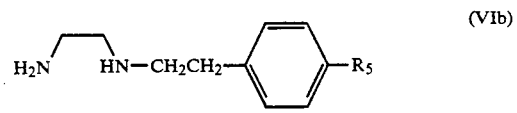

by analogy with Variant a). In the subsequent reaction step, the resulting compound is reacted with a compound of the formula $X_3$—$CH_2$—$CH_2$—$X_3$ (VIc) under N-alkylating conditions in accordance with Variant b).

Variant d): A group Y that can be oxidised to form —CO— is especially —$CH_2$—. The oxidation of corresponding compounds of formula VII is carried out using a suitable oxidising agent, preference being given to the use of tetra-$C_1$-$C_4$alkylammonium permanganates that are unsubstituted or substituted, for example by a phenyl radical, especially benzyl-triethylammonium permanganate.

The starting material of formula VII is prepared in a manner known per se. For example, a compound of formula III wherein $X_2$ is hydrogen is used as starting material and is reacted under the N-alkylating conditions described in Variant b) with a compound of the formula

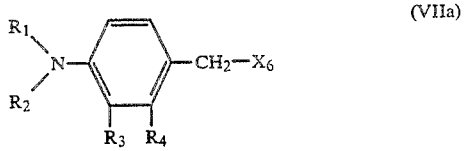

wherein $X_6$ is hydroxy or, especially, reactive esterified hydroxy, especially halogen, such as chlorine or bromine.

A compound according to the invention that is obtainable in accordance with the process or by another method can be converted in a manner known per se into a different compound according to the invention.

Compounds according to the invention wherein one of $R_1$ and $R_2$ is hydrogen and the other one is hydrogen or lower alkyl can be N-mono- or N,N-di-substituted in customary manner, for example in the manner indicated above under Variant a) or b), that is to say they can be N-acylated by means of the introduction of a lower alkanoyl, lower alkoxycarbonyl or lower alkenyloxycarbonyl group or of a phenoxycarbonyl or phenyl-lower alkoxycarbonyl group that is unsubstituted or substituted as indicated, or can be N-alkylated by means of the introduction of lower alkyl. For example, a compound of formula I wherein $R_1$ is hydrogen and $R_2$ is lower alkyl, or $R_1$ is lower alkanoyl, lower alkoxycarbonyl or lower alkenyloxycarbonyl, or phenoxycarbonyl or phenyl-lower alkoxycarbonyl that is unsubstituted or substituted as indicated and $R_2$ is hydrogen, can be N-lower alkylated to form the corresponding N,N-di-lower alkyl compound or N-lower alkanoylated or N-lower alkenylated to form the corresponding N-lower alkyl-N-lower alkanoyl, N-lower alkyl-N-lower alkoxycarbonyl, N-lower alkyl-N-lower alkenyloxycarbonyl, N-lower alkyl-N-phenoxycarbonyl or N-lower alkyl-N-phenyl-lower alkoxycarbonyl compound. The introduction of a lower alkanoyl, lower alkoxycarbonyl or lower alkenyloxycarbonyl group or of a phenoxycarbonyl or phenyl-lower alkoxycarbonyl group that is unsubstituted or substituted as indicated is effected especially by reaction with a corresponding acid anhydride, such as an acid chloride, in the presence of a basic condensation agent, preferably a Hünig base, in an ethereal solvent, such as a cycloaliphatic ether, for example tetrahydrofuran. The N-lower alkylation is effected, for example, by reaction with a lower alkyl halide or di-lower alkyl sulfate, but can also be carried out reductively by analogy with the Leuckart-Wallach (or Eschweiler-Clarke) reaction from carbonyl compounds, for example using formic acid as the reducing agent.

Resulting salts can be converted into the free compounds in a manner known per se, for example by treatment with a base, such as an alkali metal hydroxide, a metal carbonate or a metal hydrogen carbonate, or with ammonia, or another salt-forming base mentioned at the beginning, or with an acid, such as a mineral acid, for example with hydrochloric acid, or another salt-forming acid mentioned at the beginning.

Resulting salts can be converted into different salts in a manner known per se, acid addition salts for example by treatment with a suitable metal salt, such as a sodium, barium or silver salt, of a different acid in a suitable solvent in which an inorganic salt that forms is insoluble and therefore is eliminated from the reaction equilibrium, and base salts by freeing the free acid and converting it into a salt again.

The compounds of formula I, including their salts, may also be obtained in the form of hydrates or may include the solvent used for crystallisation.

In view of the close relationship between the novel compounds in free form and in the form of their salts, hereinbefore and hereinafter any reference to the free compounds or their salts should be understood as including the corresponding salts or free compounds, as appropriate and expedient.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds of the invention, especially to those starting materials resulting in the compounds of formula I that were described at the beginning as being preferred, to processes for the preparation thereof and to their use as intermediates.

The novel compounds of formula I can be used, for example, in the form of pharmaceutical compositions that comprise a therapeutically effective amount of the active ingredient, optionally together with inorganic or organic, solid or liquid pharmaceutically acceptable carriers that are suitable for enteral, for example oral, or parenteral administration. There are used, for example, tablets or gelatin capsules that comprise the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets can also comprise binders, for example magnesium aluminum silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colouring agents, flavourings and sweeteners. The novel compounds of formula I can also be used in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which, if desired, may comprise further pharmacologically active substances, are prepared in a manner known per se, for example by means of conventional mixing, granulating, confectioning, dissolving or lyophilising processes, and comprise approximately from 0.1% to 100%, especially from approximately 1% to approximately 50%, in the case of lyophilisates up to approximately 100%, active ingredient.

The invention also relates to the use of compounds of formula I, preferably in the form of pharmaceutical compositions. The dose can depend upon various factors, such as the mode of administration, the species, age and/or individual condition. The daily doses to be administered are, in the case of oral administration, from approximately 0.25 to approximately 10 mg/kg, and in the case of warm-blooded animals having a body weight of approximately 70 kg, they are preferably from approximately 20 mg to approximately 500 mg.

The following Examples illustrate the invention; temperatures are given in degrees Celsius and pressures in mbar.

EXAMPLE 1

A solution of 2 g of triethylamine in 5 ml of anhydrous dimethylformamide and then a solution of 2.15 g of chloroformic acid ethyl ester in 10 ml of methylene chloride is added dropwise to a solution, stirred at from −5° to 0°, of 3.8 g of p-propionamidobenzoic acid in 30 ml of anhydrous dimethylformamide. The reaction mixture is stirred for 30 minutes at from 0° to 5° and then a solution of 4.4 g of 1-[2-(4-chlorophenyl)ethyl]-piperazine in 25 ml of anhydrous dimethylformamide is added dropwise thereto. The suspension is stirred overnight at approximately 5° and concentrated by evaporation. 50 ml of water are added to the residue and the solution is rendered alkaline with 2N sodium hydroxide solution and extracted by shaking with methylene chloride. The combined organic phases are washed with water, dried over sodium sulfate, filtered and concentrated by evaporation. The residue is chromatographed over silica gel and the resulting oil is crystallised from acetone/diethyl ether, yielding 1-[4-(N-propionylamino)-benzoyl]-4-[2-(4-chlorophenyl)ethyl]-piperazine having a melting point of 131°–132°.

EXAMPLE 2

3 g of N,N-carbonyldiimidazole are added to a solution, stirred at room temperature, of 3.3 g of p-propionamidobenzoic acid in 15 ml of anhydrous dimethylformamide. After approximately 15 minutes the vigorous evolution of gas subsides. The reaction mixture is heated to 60° and, after 5 minutes, 3.8 g of 1-[2-(4-chlorophenyl)ethyl]-piperazine are added. The reaction mixture is stirred for 45 minutes at an oil-bath temperature of 80°–85°. The solution is cooled, 2N sodium hydroxide solution and water are added thereto and the reaction solution is stirred. 1-[4-(N-propionylamino)-benzoyl]-4-[2-(4-chlorophenyl)ethyl]-piperazine crystallises out and is filtered with suction and washed with water. It has a melting point of 131°–132°.

EXAMPLE 3

37.2 g of 1-(4-nitrobenzoyl)-4-1-[2-(4-chlorophenyl)ethyl]-piperazine are reduced at room temperature in 370 ml of tetrahydrofuran in the presence of 20 g of Raney nickel. The filtered reaction solution is concentrated by evaporation and the resulting oil is crystallised from isopropanol/petroleum ether, yielding 30 g of 1-(4-aminobenzoyl)-4-[2-(4-chlorophenyl)ethyl]-piperazine having a melting point of 111°–112°.

1-(4-nitrobenzoyl)-4-[2-(4-chlorophenyl)ethyl]-piperazine is obtained in a manner analogous to that described in Example 2. It has a melting point of 109°–110°.

EXAMPLE 4

A solution of 2 g of 1-(4-aminobenzoyl)-4-[2-(4-chlorophenyl)ethyl]-piperazine (see Example 3) in 20 ml of pyridine and 20 ml of valeric acid anhydride is left to stand overnight at room temperature. The reaction solution is poured onto 400 ml of water, 25 ml of concentrated sodium hydroxide solution are added thereto, and the whole is stirred for 1 hour at room temperature, the educt crystallising out. After decanting off the aqueous phase, methylene chloride is added and the organic phase is washed with water, dried, filtered and concentrated by evaporation, yielding 2.9 g of oil which is crystallised from diethyl ether. The resulting 1-[4-(N-valeroylamino)benzoyl]-4-[2-4-chlorophenyl)ethyl]-piperazine has a melting point of 129°–131°.

EXAMPLE 5

While stirring at room temperature, a solution of 1.8 g of 1-[4-(N-acetylamino)benzoyl]-4-(4-chlorophenylethyl)-piperazine in 20 ml of absolute dimethylformamide is added dropwise to a suspension of 0.2 g of a 50% suspension of sodium hydride in mineral oil in 20 ml of absolute dimethylformamide. After 45 minutes, a solution of 0.7 g of methyl iodide in 5 ml of absolute dimethylformamide is added dropwise thereto. Stirring is continued overnight. Dimethylformamide is distilled off in vacuo and water is added. 1-[4-(N-acetyl-N-methylamino)benzoyl]-4-[2-(4-chlorophenyl)ethyl]-piperazine having a melting point of 148°–149° crystallises out.

1-[4-(N-acetylamino)benzoyl]-4-(4-chlorophenylethyl)-piperazine is prepared from p-acetamidobenzoic acid in a manner analogous to that described in Example 2. 1-[4-(N-acetylamino)benzoyl]-4-(4-chlorophenylethyl)-piperazine can also be prepared from 1-(4-aminobenzoyl)-4-[2-(4-chlorophenyl)ethyl]-piperazine by dissolving 6.3 g of 1-(4-aminobenzoyl)-4-[2-(4-chlorophenyl)ethyl]-piperazine and 1.85 g of triethylamine in 70 ml of methylene chloride and adding dropwise thereto a solution of 1.5 g of acetyl chloride in 10 ml of methylene chloride. The reaction solution is left to stand overnight and then concentrated by evaporation. The resulting oil is taken up in ethanol, 20 ml of 2N sodium hydroxide solution are added and the reaction mixture is stirred for 4 hours at room temperature. Ethanol is then removed in vacuo and the crystals are filtered with suction and recrystallised from ethanol/diethyl ether, yielding 1-[4-(N-acetylamino)benzoyl]-4-(4-chlorophenylethyl)-piperazine having a melting point of 143°–145°.

EXAMPLE 6

1-[4-(N-methyl-N-propionylamino)benzoyl]-4-[2-(4-chlorophenyl)ethyl]-piperazine having a melting point of 138°–139° can be prepared from 2.85 g of 1-[4-(N-propionylamino)benzoyl]-4-[2-(4-chlorophenyl)ethyl]-piperazine (see Example 2) in a manner analogous to that described in Example 5.

EXAMPLE 7

In a manner analogous to that described in Example 3, 35 g of 1-(2-chloro-4-nitrobenzoyl)-4-[2-(4-chlorophenyl)ethyl]-piperazine are reduced to form 1-(4-amino-2-chlorobenzoyl)-4-[2-(4-chlorophenyl)ethyl]-piperazine having a melting point of 175°–176°.

The starting material is obtained from 2-chloro-4-nitrobenzoic acid by way of the acid chloride and subsequent reaction with 1-[2-(4-chlorophenyl)ethyl]-piperazine. It has a melting point of 115°–117°.

EXAMPLE 8

3 g of 1-(4-amino-2-chlorobenzoyl)-4-[2-(4-chlorophenyl)ethyl]-piperazine are stirred for 1 hour at room temperature in 30 ml of chloroform with 10 ml of acetic anhydride. The solution is concentrated by evaporation and water, 2N sodium hydroxide solution and 20 ml of ethyl acetate are added to the residue and the whole is stirred for 15 minutes. Filtering with suction and recrystallisation from ethanol/petroleum ether yield 1-[4-(N-acetylamino)-2-chlorobenzoyl]-4-[2-(4-chlorophenyl)ethyl]-piperazine having a melting point of 158°–160°.

EXAMPLE 9

1-[4-(N-methylamino)benzoyl]-4-[2-(4-chlorophenyl)ethyl]-piperazine can be prepared from 3 g of p-(N-methylamino)benzoic acid in a manner analogous to that described in Example 1. 1-[4-(N-methylamino)benzoyl]-4-[2-(4-chlorophenyl)ethyl]-piperazine hydrochloride having a melting point of 156°–158° is obtained therefrom by treatment with a solution of hydrogen chloride in ethyl acetate.

1-[4-(N-methylamino)benzoyl]-4-[2-(4-chlorophenyl)ethyl]-piperazine can, however, also be prepared from 3.3 g of p-(N-methylamino)benzoic acid in a manner analogous to that described in Example 2. The viscous oil that is obtained is purified by way of the hydrochloride. The recovered base is chromatographed on silica gel.

EXAMPLE 10

In a manner analogous to that described in Example 3, 20 g of 1-(3-methyl-4-nitrobenzoyl)-4-[2-(4-chlorophenyl)ethyl]-piperazine are reduced to form 1-(4-amino-3-methylbenzoyl)-4-[2-(4-chlorophenyl)ethyl]-piperazine having a melting point of 95°–100°. The hydrochloride, having a melting point of 250°, is obtained from the base.

The starting material is obtained from m-methyl-p-nitrobenzoic acid by way of the acid chloride and reaction with 1-[2-(4-chlorophenyl)ethyl]-piperazine; it has a melting point of 98°.

EXAMPLE 11

In a manner analogous to that described in Example 3, 2.3 g of 1-(2-fluoro-4-nitrobenzoyl)-4-[2-(4-chlorophenyl)ethyl]-piperazine are reduced to form 1-(4-amino-2-fluorobenzoyl)-4-[2-(4-chlorophenyl)ethyl]-piperazine having a melting point of 167°–168°.

The starting material is obtained from 2-fluoro-4-nitrobenzoic acid and reaction with 1-[2-(4-chlorophenyl)ethyl]-piperazine in the presence of N,N-carbonyldiimidazole. It has a melting point of 106°–108°.

EXAMPLE 12

1-[4-(N-ethyl-N-propionylamino)benzoyl]-4-[2-(4-chlorophenyl)ethyl]-piperazine having a melting point of 109°–110° can be prepared in a manner analogous to that described in Example 5 from 1-[4-(N-propionylamino)benzoyl]-4-[2-(4-chlorophenyl)ethyl]-piperazine (see Example 2).

EXAMPLE 13

0.8 g of 1-[4-(N-methylamino)-2-chlorobenzoyl]-4-[2-(4-chlorophenyl)ethyl]-piperazine (see Example 8) is methylated in a manner analogous to that described in Example 5 with 0.3 g of methyl iodide to form 1-[4-(N-acetyl-N-methylamino)-2-chlorobenzoyl]-4-[2-(4-chlorophenyl)ethyl]-piperazine. It has a melting point of 162°–163°.

EXAMPLE 14

1.5 g of 1-(4-amino-2-chlorobenzoyl)-4-[2-(4-chlorophenyl)ethyl]-piperazine (see Example 7) are dissolved together with 0.26 g of acetaldehyde and 0.8 ml of 5N alcoholic hydrochloric acid in 15 ml of methanol. 0.41 g of 85% NaBH₄ is added thereto and the reaction solution is stirred at room temperature for 24 hours. Water is added to the reaction solution, which is then decanted off and taken up in methylene chloride, dried and concentrated by evaporation. The oily material is chromatographed on silica gel and converted into the hydrochloride, yielding 1-[4-(N-ethylamino)-2-chlorobenzoyl]-4-[2-(4-chlorophenyl)ethyl]-piperazine hydrochloride having a melting point of 230°.

EXAMPLE 15

In a manner analogous to that described in Example 5, 0.8 g of 1-[2-chloro-4-(N-propionylamino)benzoyl]-4-[2-(4-chlorophenyl)ethyl]-piperazine is methylated with 0.29 g of methyl iodide to form 1-[4-(N-methyl-N-propionylamino)-2-chlorobenzoyl]-4-[2-(4-chlorophenyl)ethyl]-piperazine and converted into the hydrochloride having a melting point of 135°.

1-[2-chloro-4-(N-propionylamino)benzoyl]-4-[2-(4-chlorophenyl)ethyl]-piperazine is prepared from 1-(4-amino-2-chlorobenzoyl)-4-[2-(4-chlorophenyl)ethyl]-piperazine using propionic acid anhydride in chloroform. It has a melting point of 128°–130°.

EXAMPLE 16

In a manner analogous to that described in Example 5, 5 g of 1-[3-methyl-4-(N-acetylamino)benzoyl]-4-[2-(4-chlorophenyl)ethyl]-piperazine are methylated with 0.8 g of methyl iodide to form 1-[4-(N-acetyl-N-methylamino)-3-methylbenzoyl]-4-[2-(4-chlorophenyl)ethyl]-piperazine and converted into the hydrochloride having a melting point of 195°.

The starting material is prepared from 1-(4-amino-3-methylbenzoyl)-4-[2-(4-chlorophenyl)ethyl]-piperazine (see Example 10) using acetic anhydride in chloroform. It has a melting point of 156°–157°.

EXAMPLE 17

4 g of 1-(4-amino-2-chlorobenzoyl)-4-[2-(4-chlorophenyl)ethyl]-piperazine (see Example 7) are dissolved in 500 ml of anhydrous dioxane and 4 ml of chloroformic acid benzyl ester are added dropwise thereto at −15°. The reaction mixture is stirred for 1.5 hours at room temperature. The 1-[2-chloro-4-(N-benzyloxycarbonylamino)benzoyl]-4-[2-(4-chlorophenyl)ethyl]-piperazine hydrochloride having a melting point of 195° that forms is filtered off and dried.

EXAMPLE 18

In a manner analogous to that described in Example 5, the 1-[2-chloro-4-(N-benzyloxycarbonylamino)benzoyl]-4-[2-(4-chlorophenyl)ethyl]-piperazine hydrochloride obtained in accordance with Example 17 is methylated with 0.8 g of methyl iodide, yielding 1-[2-chloro-4-(N-benzyloxycarbonyl-N-methylamino)benzoyl]-4-[2-(4-chlorophenyl)ethyl]-piperazine hydrochloride.

EXAMPLE 19

The 1-[2-chloro-4-(N-benzyloxycarbonyl-N-methylamino)benzoyl]-4-[2-(4-chlorophenyl)ethyl]-piperazine hydrochloride obtained in accordance with Example 18 is dissolved in 15 ml of methanol and debenzylated in the presence of 0.2 g of 10% palladium-on-carbon, yielding 1-[4-(N-methylamino)-2-chlorobenzoyl]-4-[2-(4-chlorophenyl)ethyl]-piperazine having a melting point of 200°.

EXAMPLE 20

In a manner analogous to that described in Example 5, 1-[4-(N-acetyl-N-ethylamino)benzoyl]-4-[2-(4-chlorophenyl)ethyl]-piperazine having a melting point of 133°–134° can be prepared from 1-[4-(N-acetylamino)benzoyl]-4-[2-(4-chlorophenyl)ethyl]-piperazine.

EXAMPLE 21

In a manner analogous to that described in Example 2, 1-[4-(N-methylamino)benzoyl]-4-[2-(4-fluorophenyl)ethyl]-piperazine can be prepared from 1.2 g of 4-methylaminobenzoic acid and 1.5 g of 1-[2-(4-fluorophenyl)ethyl]-piperazine and crystallised in the form of the hydrochloride having a melting point of 207°–208°.

EXAMPLE 22

In a manner analogous to that described in Example 2, 1-[4-(N-methylamino)benzoyl]-4-[2-(4-bromophenyl)ethyl]-piperazine having a melting point of 92°–93.5° is prepared from 1.66 g of 4-methylaminobenzoic acid and 1.7 g of 1-[2-(4-bromophenyl)ethyl]-piperazine.

EXAMPLE 23

In a manner analogous to that described in Example 2, 1-[4-(N-ethylamino)benzoyl]-4-[2-(4-chlorophenyl)ethyl]-piperazine having a melting point of 99°–101° is prepared from 1.65 g of 4-ethylaminobenzoic acid and 2.2 g of 1-[2-(4-chlorophenyl)ethyl]-piperazine.

EXAMPLE 24

In a manner analogous to that described in Example 2, 1-(4-nitro-3-bromobenzoyl)-4-[2-(4-chlorophenyl)ethyl]-piperazine is prepared from 4.7 g of 4-nitro-3-bromobenzoic acid and 1-[2-(4-chlorophenyl)ethyl]-piperazine and, as described in Example 3, reduced in the presence of Raney nickel to form 1-(4-amino-3-bromobenzoyl)-4-[2-(4-chlorophenyl)ethyl]-piperazine having a melting point of 120°–123°.

EXAMPLE 25

In a manner analogous to that described in Example 5, 1-[4-(N-acetyl-N-ethylamino)benzoyl]-4-[2-(4-bromophenyl)ethyl]-piperazine having a melting point of 131°–131.5° is prepared from 1-(4-acetylaminobenzoyl)-4-[2-(4-bromophenyl)ethyl]-piperazine and 1.6 g of ethyl iodide.

In a manner analogous to that described in Example 2, the starting material is obtained from 4-acetamidobenzoic acid and 1-[2-(4-bromophenyl)ethyl]-piperazine having a melting point of 193°–194°.

EXAMPLE 26

While stirring at room temperature, 0.45 g of N-ethyldiisopropylamine is added dropwise to a solution of 1.03 g of 1-[4-N-methylaminobenzoyl]-4-[2-(4-chlorophenyl)ethyl]-piperazine in 15 ml of anhydrous tetrahydrofuran and then 1.69 ml of 33% chloroformic acid benzyl ester in toluene are added dropwise. The reaction solution is stirred for 30 minutes at room temperature and then concentrated by evaporation using a rotary evaporator. The oily residue is taken up in ethyl acetate, washed with water and 5% soda solution, dried with magnesium sulfate, filtered and concentrated by evaporation. After digestion with ether, 1-[4-(N-benzyloxycarbonyl-N-methyl-amino)benzoyl]-4-[2-(4-chlorophenyl)ethyl]-piperazine having a melting point of 78°–79° crystallises.

EXAMPLE 27

The following compounds are prepared in a manner analogous to that described in Example 26:

1-[4-(N-benzyloxycarbonyl-N-butylamino)benzoyl]-4-[2-(4-chlorophenyl)ethyl]-piperazine having a melting point of 146°–148° is obtained from 0.70 g of 1-[4-(N-butylamino)benzoyl]-4-[2-(4-chlorophenyl)ethyl]-piperazine.

1-[4-(N-benzyloxycarbonylamino)-3-methylbenzoyl]-4-[2-(4-chlorophenyl)ethyl]-piperazine having a melting point of 113°–115° is obtained from 1.06 g of 1-[4-amino-3-methylbenzoyl]-4-[2-(4-chlorophenyl)ethyl]-piperazine.

1-[4-(N-benzyloxycarbonyl-N-ethylamino)benzoyl]-4-[2-(4-bromophenyl)ethyl]-piperazine having a melting point of 61°–62° is obtained from 0.74 g of 1-[4-(N-ethylamino)benzoyl]-4-[2-(4-bromophenyl)ethyl]-piperazine.

1-[4-(N-benzyloxycarbonyl-N-methylamino)benzoyl]-4-[2-(4-bromophenyl)ethyl]-piperazine having a melting point of 81°–82° is obtained from 0.74 g of 1-[4-(N-methylamino)benzoyl]-4-[2-(4-bromophenyl)ethyl]-piperazine.

1-[4-(N-benzyloxycarbonylamino)benzoyl]-4-[2-(4-fluorophenyl)ethyl]-piperazine having a melting point of 158°–159° is obtained from 1.04 g of 1-[4-aminobenzoyl]-4-[2-(4-fluorophenyl)ethyl]-piperazine.

1-[4-(N-benzyloxycarbonylamino)-2-fluorobenzoyl]-4-[2-(4-chlorophenyl)ethyl]-piperazine having a melting point of 140°–141° is obtained from 0.60 g of 1-[4-amino-2-fluorobenzoyl]-4-[2-(4-chlorophenyl)ethyl]-piperazine.

1-[4-(N-benzyloxycarbonylamino)-2-bromobenzoyl]-4-[2-(4-chlorophenyl)ethyl]-piperazine having a melting point of 128°–130° is obtained from 0.45 g of 1-[4-amino-2-bromobenzoyl]-4-[2-(4-chlorophenyl)ethyl]-piperazine.

1-[4-(N-benzyloxycarbonyl-N-{2-dimethylaminoethyl}amino)benzoyl]-4-[2-(4-chlorophenyl)ethyl]-piperazine hydrochloride having a melting point of 133°–136° is obtained from 0.62 g of 1-[4-(N-{2-dimethylaminoethyl}amino)benzoyl]-4-[2-(4-chlorophenyl)ethyl]-piperazine.

The starting material can be prepared from 1-[4-(amino)benzoyl]-4-[2-(4-chlorophenyl)ethyl]-piperazine and 2-dimethylaminoacetaldehyde in a manner analogous to that described in Example 14.

EXAMPLE 28

8 g of 1-[4-aminobenzoyl]-4-[2-(4-chlorophenyl)ethyl]-piperazine are dissolved in 200 ml of dioxane. 8.7 g of chloroformic acid benzyl ester in the form of a 50% solution in toluene are added dropwise thereto at 15°. After 2 hours at room temperature, the reaction mixture is diluted with water, dioxane is distilled off and the aqueous phase is rendered alkaline with 2N sodium hydroxide solution and extracted by shaking with ethyl acetate. The oil obtained from the ethyl acetate is crystallised from alcohol and ether, yielding 1-[4-(N-benzyloxycarbonylamino)benzoyl]-4-[2-(4-chlorophenyl)ethyl]-piperazine having a melting point of 149°–150°.

EXAMPLE 29

90 g of 1-[4-(N-acetylamino)benzoyl]-4-[2-(4-chlorophenyl)ethyl]-piperazine and 2.8 g of 4-dimethylaminopyridine are suspended in 800 ml of acetonitrile. While cooling externally, a solution of 62 g of butoxycarbonyl anhydride in 100 ml of acetonitrile is added dropwise thereto in the course of 20 minutes. The suspension is stirred overnight at room temperature and then 47.4 g of 2-diethylaminoethylamine in 50 ml of acetonitrile are added dropwise thereto (1-[4-(N-butoxycarbonyl-N-acetylamino)benzoyl]-4-[2-(4-chlorophenyl)ethyl]-piperazine which occurs as intermediate is hydrolysed in accordance with L. Grehn et al., Acta Chem. Scand. B41, 18–23, 1987). The resulting clear solution is stirred overnight. The reaction solution is concentrated by evaporation. The oily residue is extracted by shaking with ethyl acetate, concentrated by evaporation and crystallised from ether, yielding 1-[4-(N-tert-butoxycarbonylamino)benzoyl]-4-[2-(4-chlorophenyl)ethyl]-piperazine having a melting point of 127°–128°.

EXAMPLE 30

1 g of 1-[4-aminobenzoyl]-4-[2-(4-chlorophenyl)ethyl]-piperazine and 0.4 g of Hünig base (=N-ethyldiisopropylamine) are dissolved in 15 ml of tetrahydrofuran. A solution of 0.75 g of chloroformic acid 4-nitrobenzyl ester in 5 ml of tetrahydrofuran is added dropwise thereto. The reaction solution is stirred for 3.5 hours at room temperature and for 2 hours at a bath temperature of 55°. The solution is concentrated by evaporation and the residue is taken up in methylene chloride and washed with water. Colourless crystals of 1-[4-(N-4-nitrobenzyloxycarbonylamino)benzoyl]-4-[2-(4-chlorophenyl)ethyl]-piperazine having a melting point of 146°–148° are obtained from alcohol.

EXAMPLE 31

The following compounds are prepared in a manner analogous to that described in Example 30:

1-[4-(N-phenoxycarbonylamino)benzoyl]-4-[2-(4-chlorophenyl)ethyl]-piperazine having a melting point of 174°–175° is prepared from 1 g of 1-[4-aminobenzoyl]-4-[2-(4-chlorophenyl)ethyl]-piperazine;

1-[4-(N-allyloxycarbonylamino)benzoyl]-4-[2-(4-chlorophenyl)ethyl]-piperazine having a melting point of 136°–138° is prepared from 1 g of 1-[4-aminobenzoyl]-4-[2-(4-chlorophenyl)ethyl]-piperazine;

1-[4-(N-ethoxycarbonylamino)benzoyl]-4-[2-(4-chlorophenyl)ethyl]-piperazine having a melting point of 161°–162° is prepared from 1 g of 1-[4-aminobenzoyl]-4-[2-(4-chlorophenyl)ethyl]-piperazine.

EXAMPLE 32

3.0 g of 1-(4-amino-2-chloro-benzoyl)-4-[2-(4-chlorophenyl)ethyl]-piperazine are stirred for 2 h together with 10 ml butyric anhydride in 50 ml chloroform at room temperature (RT). The solvent is evaporated, the residue is rendered alkaline with NaOH and extracted with ethyl acetate. The organic phase is concentrated by evaporation, and the residue is crystallised from toluene; thus 1-(4-N-butyrylamino-2-chloro-benzoyl)-4-[2-(4-chlorophenyl)ethyl]-piperazine is obtained, m.p. 135°–137°.

EXAMPLE 33

1.7 g of 1-[4-(N-acetylamino)benzoyl]-4-[2-(4-chlorophenyl)ethyl]-piperazine, dissolved in 20 ml DMF, is added to a suspension of 0.23 g 50% NaH in 20 ml DMF. After 1.5 h of stirring at RT, 0.97 g n-propyl iodide, dissolved in 5 ml DMF, are added dropwise. The reaction mixture is stirred overnight. DMF is distilled off in vacuo, water is added, and the product is extracted with ethyl acetate. The organic phase is concentrated by evaporation, and the residue is crystallised from ether/petroleum ether; thus 1-[4-(N-acetyl-N-propylamino)benzoyl]-4-[2-(4-chlorophenyl)ethyl]-piperazine is obtained m.p. 112°–113°.

EXAMPLE 34

1.7 g of 1,1-carbonyldiimidazole is added to a solution of 1.9 g of 4-butylaminobenzoic acid in 25 ml DMF. The mixture is stirred for 5 min at RT, then for 15 min at 100°. The mixture is allowed to cool down a little bit; then 2.2 g of N-[2-(4-chlorophenethyl)]-piperazine is added under stirring. The mixture is stirred for 1 h at 100°, is then allowed to cool down and poured onto 150 ml of water. The product is extracted with dichloromethane, the organic phase is dried and concentrated by evaporation. The oily residue obtained is purified by chromatography on 60 g of silicagel using a mixture of dichloromethane/acetone 9:1 as eluant. The viscous oil obtained is dried in vacuo at 70°. After one week, the product being 1-[4-(N-butylamino)benzoyl]-4-[2-(4-chlorophenyl)ethyl]-piperazine crystallises, m.p. 79°–80°.

EXAMPLE 35

In a manner analogous to that described in Example 5, 1.6 g of 1-(4-acetylaminobenzoyl)-4-[2-(4-bromophenyl)ethyl]-piperazine, dissolved in 15 ml DMF, are treated first with 0.2 g NaH in 10 ml DMF and then with 0.6 g methyl iodide in 5 ml DMF. The crude product is crystallised from ether. Thus 1-[4-(N-acetyl-N-methylamino)benzoyl]-4-[2-(4-bromophenyl)ethyl]-piperazine is obtained, m.p. 161°–162°.

EXAMPLE 36

Tablets, each comprising 50 mg of 1-(4-amino-2-chlorobenzoyl)-4-[2-(4-chlorophenyl)ethyl]-piperazine or of a salt, for example the hydrochloride, thereof, can be prepared as follows:

| Composition (for 10000 tablets): | |
|---|---|
| active ingredient | 500.0 g |
| lactose | 500.0 g |
| potato starch | 352.0 g |
| gelatin | 8.0 g |
| talcum | 60.0 g |
| magnesium stearate | 10.0 g |
| silica (highly dispersed) | 20.0 g |
| ethanol | q.s. |

The active ingredient is mixed with the lactose and 292 g of the potato starch, and the mixture is moistened with an ethanolic solution of the gelatin and granulated through a sieve. After drying, the remaining potato starch, the magnesium stearate, the talcum and the silica are mixed in and the mixture is compressed to form tablets which each weigh 145.0 mg and comprise 50.0 mg of active ingredient, and which may, if desired, be provided with breaking notches for finer adaptation of the dose.

EXAMPLE 37

Gelatin dry-filled capsules, containing 100 mg of active ingredient, for example 1-(4-amino-2-chlorobenzoyl)-4-[2-(4-chlorophenyl)ethyl]-piperazine, or of a salt, for example the hydrochloride, thereof, can be prepared, for example, as follows:

| Composition (for 1000 capsules) | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve having a mesh size of 0.2 mm. The two components are intimately mixed. Then first the lactose is added through a sieve having a mesh size of 0.6 mm and then the microcrystalline cellulose is added through a sieve having a mesh size of 0.9 mm. The mixture is again intimately mixed for 10 minutes. Finally, the magnesium stearate is added through a sieve having a mesh size of 0.8 mm. After further mixing for 3 minutes, gelatin dry-fill capsules of size 0 are each filled with 390 mg of the resulting formulation.

EXAMPLE 38

Film-coated tablets, each comprising 100 mg of 1-(4-amino-2-chlorobenzoyl)-4-[2-(4-chlorophenyl)ethyl]-piperazine or of a salt, for example the hydrochloride, thereof, can be prepared as follows:

| Composition (for 1000 tablets): | |
| --- | --- |
| active ingredient | 100.00 g |
| lactose | 100.00 g |
| corn starch | 70.00 g |
| talcum | 8.50 g |
| calcium stearate | 1.50 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, and the mixture is moistened with a paste, prepared from 15 g of the corn starch and water (with heating), and granulated. The granules are dried, the remaining corn starch, the talcum and the calcium stearate are added and mixed with the granules. The mixture is compressed to form tablets (weight: 280 mg), which are film-coated with a solution of the hydroxypropylmethylcellulose and the shellac in methylene chloride; final weight of the film-coated tablet: 283 mg.

EXAMPLE 39

A 0.2% injection or infusion solution of 1-(4-amino-2-chlorobenzoyl)-4-[2-(4-chlorophenyl)ethyl]-piperazine or of a salt, for example the hydrochloride, thereof can be prepared, for example, as follows:

| Composition (for 1000 ampoules) | |
| --- | --- |
| active ingredient | 5.0 g |
| sodium chloride | 22.5 g |

| -continued | |
| --- | --- |
| Composition (for 1000 ampoules) | |
| phosphate buffer pH = 7.4 | 300.0 g |
| demineralised water | ad 2500.0 ml |

The active ingredient and the sodium chloride are dissolved in 1000 ml of water and filtered through a micro-filter. The buffer solution is added, and the mixture is made up to 2500 ml with water. To prepare unit dose forms, 1.0 or 2.5 ml are introduced into glass ampoules, each of which then contains 2.0 or 5.0 mg, respectively, of active ingredient.

EXAMPLE 40

In a manner analogous to that described in Examples 36 to 39, it is also possible to prepare tablets each comprising 25 mg of another of the compounds mentioned in Examples 1 to 35.

What is claimed is:

1. A N-benzoyl-N'-(2-phenylethyl)-piperazine of formula I

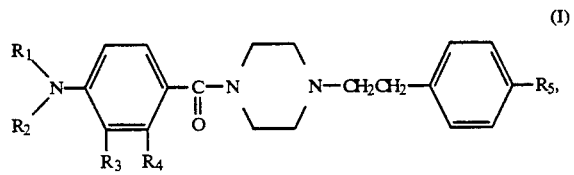

wherein (a) $R_1$ is hydrogen, lower alkanoyl, lower alkoxycarbonyl or lower alkenyloxycarbonyl, or a phenoxycarbonyl or phenyl-lower alkoxycarbonyl group that is unsubstituted or substituted by lower alkyl, lower alkoxy, halogen having an atomic number of up to and including 35, trifluoromethyl, nitro and/or by amino and $R_2$ is hydrogen or lower alkyl which is not interrupted by nitrogen; or (b) $R_1$ is hydrogen, lower alkyl, lower alkanoyl, lower alkoxycarbonyl or lower alkenyloxycarbonyl, or a phenoxycarbonyl or phenyl-lower alkoxycarbonyl group that is unsubstituted or substituted by lower alkyl, lower alkoxy, halogen having an atomic number of up to and including 35, trifluoromethyl, nitro and/or by amino and $R_2$ is lower alkyl which is interrupted by nitrogen; $R_3$ and $R_4$, independently of one another, are hydrogen, lower alkyl or halogen having an atomic number of up to and including 35 and $R_5$ is halogen having an atomic number of up to and including 35, with the proviso that, in compounds of formula I wherein $R_5$ is chlorine, $R_1$ is acetyl and $R_2$ is hydrogen, at least one of the radicals $R_3$ and $R_4$ is other than hydrogen, or a pharmaceutically acceptable salt thereof.

2. A N-benzoyl-N'-(2-phenylethyl)-piperazine of formula I

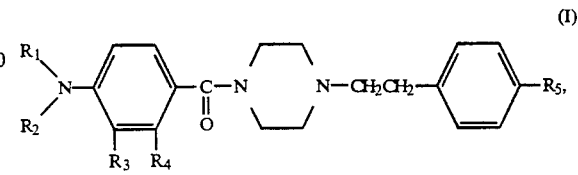

wherein $R_1$ is hydrogen, lower alkanoyl, lower alkoxycarbonyl or lower alkenyloxycarbonyl, or a phenoxycarbonyl or phenyl-lower alkoxycarbonyl group that is unsubstituted or substituted by lower alkyl, lower alkoxy, halogen having an atomic number of up to and including 35, trifluoromethyl, nitro and/or by amino and $R_2$ is hydrogen or lower alkyl which is or is not interrupted by a nitrogen atom; $R_3$ and $R_4$, independently of one another, are hydrogen, lower alkyl or halogen having an atomic number of up to and including 35 and $R_5$ is halogen having an atomic number of up to and including 35, with the proviso that, in compounds of formula I wherein $R_5$ is chlorine, $R_1$ is acetyl and $R_2$ is hydrogen, at least one of the radicals $R_3$ and $R_4$ is other than hydrogen, or a pharmaceutically acceptable salt thereof.

3. A compound according to claim 2 of formula I wherein $R_1$ is hydrogen, or lower alkanoyl, and $R_2$ is hydrogen or lower alkyl, or a pharmaceutically acceptable salt thereof.

4. A compound according to claim 1 of formula I wherein (a) $R_1$ is hydrogen, $C_2$-$C_7$alkanoyl, $C_1$-$C_7$alkoxycarbonyl or $C_2$-$C_7$alkenyloxycarbonyl, or a phenoxycarbonyl or phenyl-$C_1$-$C_7$alkoxycarbonyl group that is unsubstituted or substituted by lower alkyl, lower alkoxy, halogen having an atomic number of up to and including 35, trifluoromethyl, nitro and/or by amino and $R_2$ is hydrogen or $C_1$-$C_4$alkyl; or (b) $R_1$ is hydrogen, $C_1$-$C_4$alkyl, $C_2$-$C_7$alkanoyl, $C_1$-$C_7$alkoxycarbonyl or $C_2$-$C_7$alkenyloxycarbonyl, or a phenoxycarbonyl or phenyl-$C_1$-$C_7$alkoxycarbonyl group that is unsubstituted or substituted by lower alkyl, lower alkoxy, halogen having an atomic number of up to and including 35, trifluoromethyl, nitro and/or by amino and $R_2$ is N-$C_1$-$C_4$alkylamino-$C_2$-$C_7$alkyl or N,N-di-$C_1$-$C_4$alkylamino-$C_1$-$C_7$alkyl; one of the radicals $R_3$ and $R_4$ is hydrogen, $C_1$-$C_4$alkyl or halogen having an atomic number of up to and including 35 and the other is hydrogen and $R_5$ is halogen having an atomic number of up to and including 35, or a pharmaceutically acceptable salt thereof.

5. A compound according to claim 2 of formula I wherein $R_1$ is hydrogen or $C_2$-$C_7$alkanoyl, $R_2$ is hydrogen or $C_1$-$C_4$alkyl, one of the radicals $R_3$ and $R_4$ is hydrogen, $C_1$-$C_4$alkyl or halogen and the other is hydrogen, or a pharmaceutically acceptable salt thereof.

6. A compound according to claim 2 of formula I wherein $R_1$ is hydrogen, $C_2$-$C_7$alkanoyl, $C_1$-$C_4$alkoxycarbonyl, $C_3$-$C_5$alkenyloxycarbonyl, phenoxycarbonyl or phenyl-$C_1$-$C_4$alkoxycarbonyl, $R_2$ is hydrogen, $C_1$-$C_4$alkyl or N,N-di-$C_1$-$C_4$alkylamino-$C_1$-$C_7$alkyl, one of the radicals $R_3$ and $R_4$ is hydrogen, $C_1$-$C_4$alkyl or halogen and the other is hydrogen, or a pharmaceutically acceptable salt thereof.

7. A compound according to claim 2 of formula I wherein $R_1$ is $C_1$-$C_4$alkanoyl and $R_2$ is hydrogen or $C_1$-$C_4$alkyl or $R_1$ and $R_2$ are both hydrogen; $R_3$ is hydrogen or $C_1$-$C_4$alkyl and $R_4$ is hydrogen or $R_3$ is hydrogen and $R_4$ is halogen, or a pharmaceutically acceptable salt thereof.

8. A compound according to claim 2 of formula I wherein $R_1$ is hydrogen or $C_1$-$C_4$alkanoyl and $R_2$ is hydrogen; and $R_3$ is $C_1$-$C_4$alkyl and $R_4$ is hydrogen, or $R_3$ is hydrogen and $R_4$ is halogen, or a pharmaceutically acceptable salt thereof.

9. A compound according to claim 2 of formula I wherein $R_1$ is hydrogen, $R_2$ is hydrogen or $C_1$-$C_4$alkyl, and one of the radicals $R_3$ and $R_4$ is hydrogen, $C_1$-$C_4$alkyl or halogen and the other is hydrogen, or a pharmaceutically acceptable salt thereof.

10. A compound according to claim 2 of formula I wherein $R_1$ is $C_2$-$C_7$alkanoyl, $R_2$ is hydrogen or $C_1$-$C_4$alkyl, $R_3$ is hydrogen and $R_4$ is hydrogen or halogen, or a pharmaceutically acceptable salt thereof.

11. A compound according to claim 2 of formula I wherein $R_1$ is hydrogen and $R_2$ is hydrogen or $C_1$-$C_4$alkyl, $R_3$ is hydrogen or $C_1$-$C_4$alkyl, $R_4$ is hydrogen, fluorine or chlorine and $R_5$ is fluorine, chlorine or bromine, or a pharmaceutically acceptable salt thereof.

12. A compound of formula I according to claim 2 wherein $R_1$ is $C_2$-$C_7$alkanoyl or phenyl-$C_1$-$C_4$alkoxycarbonyl and $R_2$ is hydrogen, $C_1$-$C_4$alkyl or N,N-di-$C_1$-$C_4$alkylamino-$C_1$-$C_7$alkyl, $R_3$ and $R_4$ are hydrogen and $R_5$ is chlorine, or a pharmaceutically acceptable salt thereof.

13. A compound of formula I according to claim 2 wherein $R_1$ is $C_2$-$C_7$alkanoyl, $R_2$ is hydrogen or $C_1$-$C_4$alkyl, $R_3$ and $R_4$ are hydrogen and $R_5$ is chlorine, or a pharmaceutically acceptable salt thereof.

14. A compound of formula I according to claim 2 wherein $R_1$ is hydrogen, $R_2$ is hydrogen or $C_1$-$C_4$alkyl, $R_3$ is hydrogen and $R_4$ is fluorine or chlorine, or $R_3$ is methyl and $R_4$ is hydrogen, and $R_5$ is chlorine, or a pharmaceutically acceptable salt thereof.

15. 1-[4-(N-propionylamino)benzoyl]-4-[2-(4-chlorophenyl)ethyl]-piperazine or 1-(4-aminobenzoyl)-4-[2-(4-chlorophenyl)ethyl]-piperazine according to claim 2 or a pharmaceutically acceptable salt thereof.

16. 1-[4-(N-methylamino)benzoyl]-4-[2-(4-bromophenyl)ethyl]-piperazine or a pharmaceutically acceptable salt thereof.

17. A pharmaceutical composition for treating pain comprising an effective amount of a compound according to claim 1 or a pharmaceutically acceptable salt thereof and a pharmaceutically acceptable carrier.

18. A pharmaceutical composition for treating pain comprising an effective amount of a compound according to claim 16 or a pharmaceutically acceptable salt thereof and a pharmaceutically acceptable carrier.

19. A method for treating pain in a warm-blooded animal in need thereof, comprising administering to said animal an effective amount of a compound according to claim 1 or a pharmaceutically acceptable salt thereof.

20. A method for treating pain in a warm-blooded animal in need thereof, comprising administering to said animal an effective amount of a compound according to claim 16 or a pharmaceutically acceptable salt thereof.

* * * * *